(12) United States Patent
Ishizaki

(10) Patent No.: US 9,829,080 B2
(45) Date of Patent: Nov. 28, 2017

(54) DRIVING FORCE TRANSMISSION MECHANISM

(71) Applicant: OLYMPUS CORPORATION, Tokyo (JP)

(72) Inventor: Ryosuke Ishizaki, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/347,885

(22) Filed: Nov. 10, 2016

(65) Prior Publication Data

US 2017/0059009 A1 Mar. 2, 2017

Related U.S. Application Data

(63) Continuation of application No. PCT/JP2015/076343, filed on Sep. 16, 2015.

(30) Foreign Application Priority Data

Mar. 13, 2015 (JP) .................. 2015-051261

(51) Int. Cl.
*A61B 1/00* (2006.01)
*A61B 1/04* (2006.01)
(Continued)

(52) U.S. Cl.
CPC .............. *F16H 7/02* (2013.01); *A61B 1/005* (2013.01); *A61B 1/0016* (2013.01); *A61B 1/00071* (2013.01); *A61B 1/00156* (2013.01); *A61B 1/04* (2013.01); *A61B 1/06* (2013.01); *F16H 57/01* (2013.01); *G02B 23/2476* (2013.01);
(Continued)

(58) Field of Classification Search
CPC ......... A61B 1/0016; A61B 1/005; A61B 1/06; A61B 1/04; A61B 1/31; F16H 7/02; F16H 57/01; G02B 23/2476
See application file for complete search history.

(56) References Cited

U.S. PATENT DOCUMENTS

2012/0029281 A1 2/2012 Frassica et al.

FOREIGN PATENT DOCUMENTS

| CN | 103889303 A | 6/2014 |
|---|---|---|
| JP | H05-037726 U | 5/1993 |

(Continued)

OTHER PUBLICATIONS

International Search Report dated Dec. 22, 2015 issued in PCT1JP2015/076343.
(Continued)

*Primary Examiner* — Timothy J Neal
(74) *Attorney, Agent, or Firm* — Scully, Scott, Murphy & Presser, P.C.

(57) ABSTRACT

A driving force transmission mechanism includes a first member being arranged inside an insertion section of an insertion apparatus extending along a predetermined axis, a second member being arranged to be positioned on a movement locus in a circumferential direction of the first member. The mechanism includes a cover member as an outer coat of the insertion section. The cover member is arranged between the first member and the second member to come in contact with at least the second member. The mechanism also includes an indicator being provided on the cover member. The indicator indicates in the cover member a change in state of a surface in contact with the second member.

15 Claims, 8 Drawing Sheets

(51) Int. Cl.
*F16H 7/02* (2006.01)
*A61B 1/005* (2006.01)
*A61B 1/06* (2006.01)
*F16H 57/01* (2012.01)
*G02B 23/24* (2006.01)
*H04N 5/225* (2006.01)

(52) U.S. Cl.
CPC ...... *F16H 2057/014* (2013.01); *H04N 5/2256* (2013.01); *H04N 2005/2255* (2013.01)

(56) References Cited

FOREIGN PATENT DOCUMENTS

| | | |
|---|---|---|
| JP | 2003-154148 A | 5/2003 |
| JP | 2012-080972 A | 4/2012 |
| JP | 2014-524807 A | 9/2014 |
| WO | 2013/038720 A1 | 3/2013 |

OTHER PUBLICATIONS

Chinese Office Action dated Jul. 20, 2017 in Chinese Patent Application No. 201580022692.2.

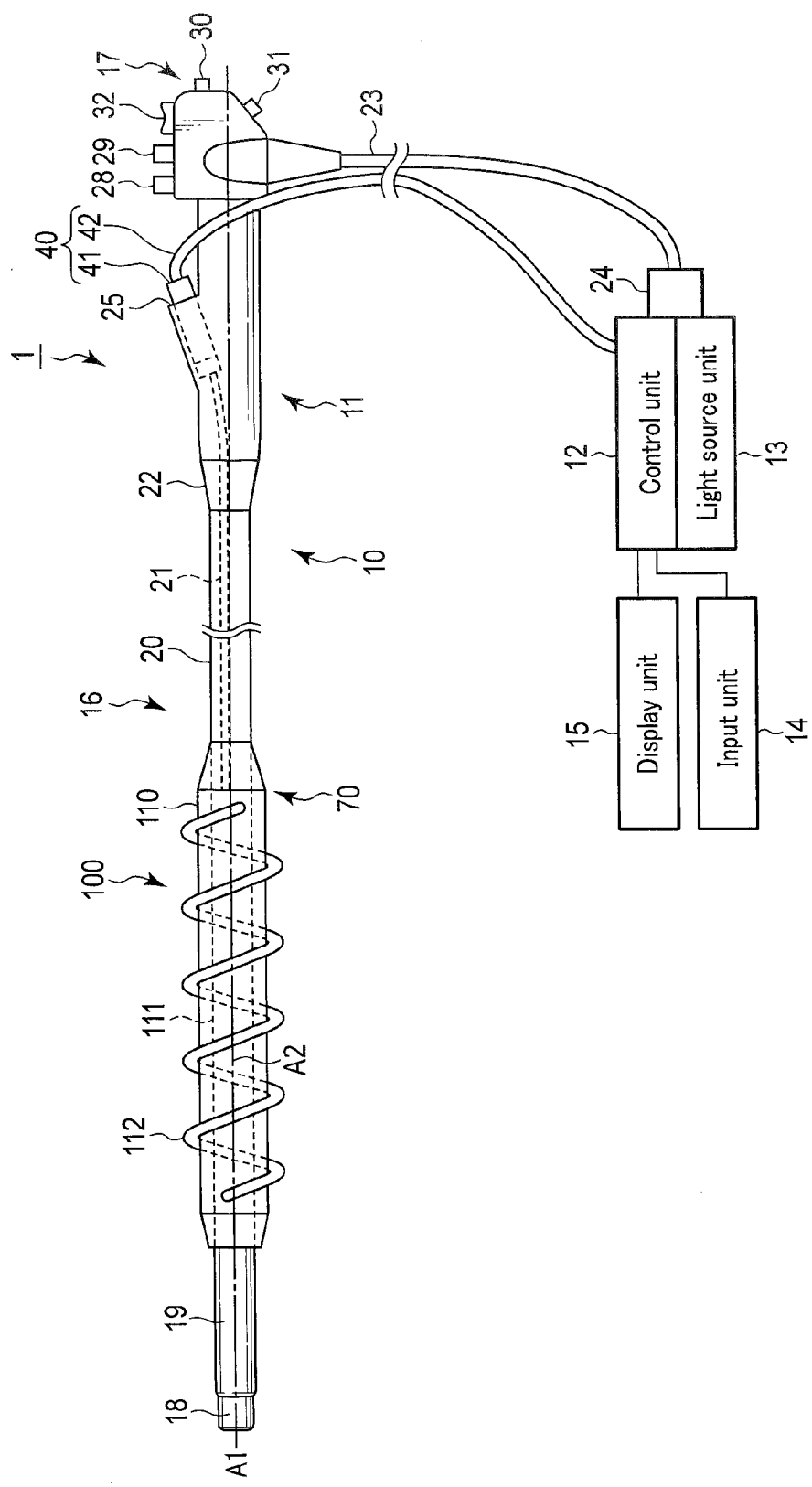
F I G. 1

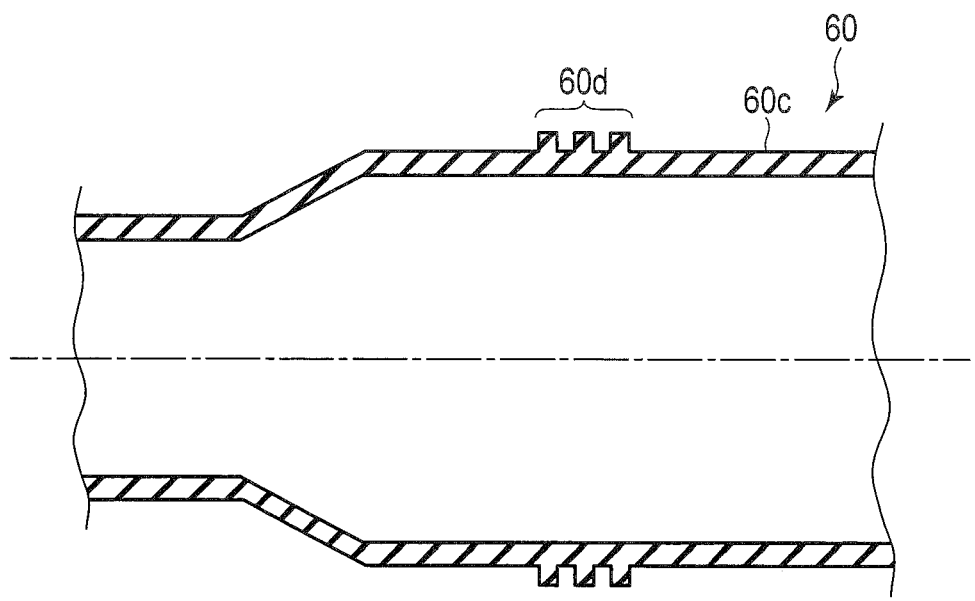
F I G. 9
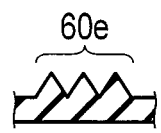
F I G. 10
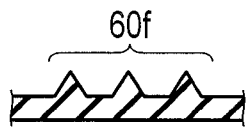
F I G. 11

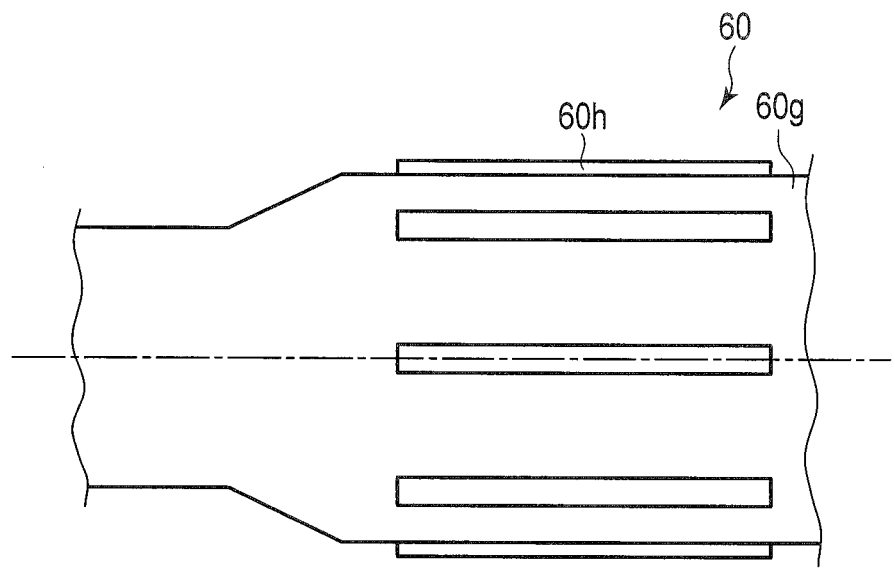
F I G. 12
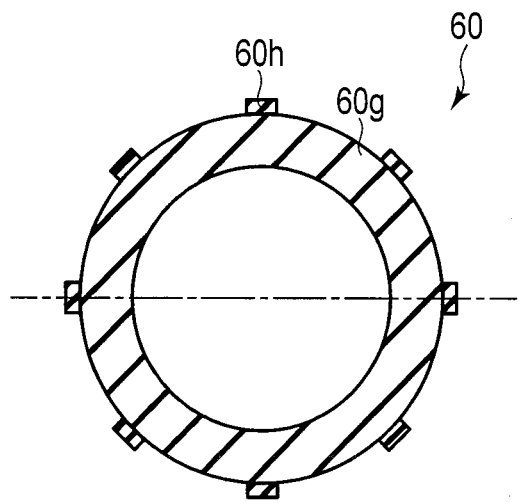
F I G. 13

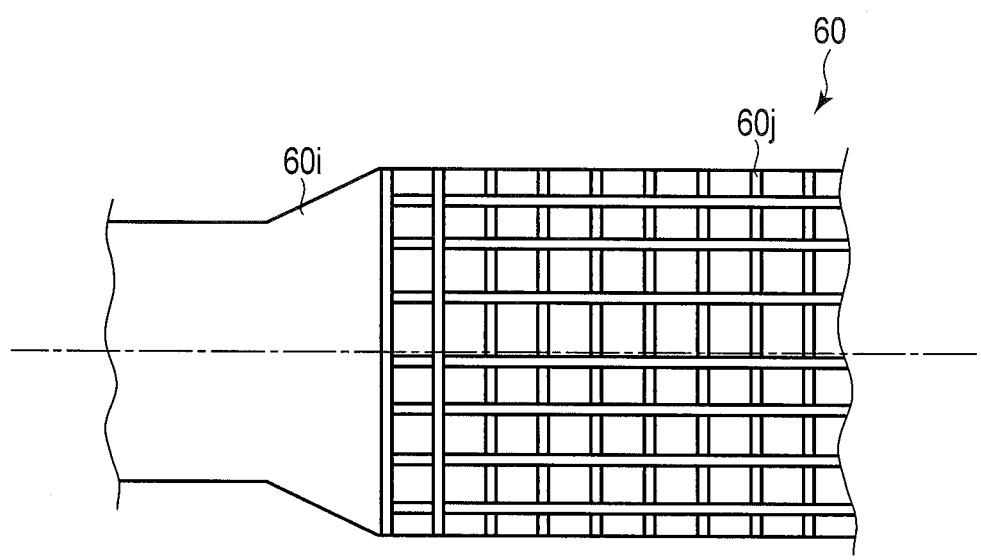
F I G. 14

DRIVING FORCE TRANSMISSION MECHANISM

CROSS-REFERENCE TO RELATED APPLICATIONS

This application is a Continuation Application of PCT Application No. PCT/JP2015/076343, filed Sep. 16, 2015 and based upon and claiming the benefit of priority from prior the Japanese Patent Application No. 2015-051261, filed Mar. 13, 2015, the entire contents of all of which are incorporated herein by references.

BACKGROUND OF THE INVENTION

1. Field of the Invention

The present invention relates to a driving force transmission mechanism which comprises a first member that is moved by a driving force from a driving source, a second member that is moved by coming in contact with the first member when the first member is being moved, and a cover member that is arranged between the first member and the second member.

2. Description of the Related Art

An endoscope apparatus which comprises an endoscope comprising an insertion section, and an insertion assisting tool attached to the outer periphery of the insertion section to assist its insertion is known. For example, International Publication No. 2013/038720 discloses an endoscope apparatus comprising an endoscope comprising an insertion section extending in a longitudinal axis direction, a drive ring attached to the insertion section, and a tubular drive tube attached to the outer periphery of the drive ring. The drive ring and the drive tube are attached so as to be coaxial with the insertion section of the endoscope.

In the endoscope apparatus, a flexible drive shaft is arranged on the insertion section of the endoscope. The drive ring comprises a stator, a rotor which is rotatable around the stator and is detachably connected to the drive tube, a rotation gear which is configured to transmit rotary motion from the drive shaft to the rotor in order to rotate the drive tube, and a cylindrical cover member which covers the outer periphery of the stator.

On the outer periphery of the rotation gear is provided a plurality of transfer rollers (internal rollers), and on the inner surface of the rotor is provided a plurality of housing rollers (external rollers). The cover member is fixed on the surface of the stator and is arranged between the transportation rollers and the housing rollers. Furthermore, on the outer periphery of the drive tube is provided a spirally formed fin.

When observing a serpentine tubular organ, etc. such as a large intestine or a small intestine using the above-mentioned endoscope apparatus, the drive tube is rotated in its longitudinal axis direction by rotating the transfer rollers and the housing rollers by the driving force transmitted from the drive shaft and the rotation gear. The insertion section advances while the spiral fin of the rotating drive tube pushes the wall, such as the intestinal wall, to which it abuts. In this manner, the insertion section is assisted to be inserted into the deep site of the organ.

BRIEF SUMMARY OF THE INVENTION

One embodiment of the present invention is a driving force transmission mechanism comprising a first member which is connected to a driving source and is moved in a circumferential direction about a predetermined axis by a driving force from the driving source, a second member which is movable in a circumferential direction about the predetermined axis and is arranged to be positioned on a movement locus in the circumferential direction of the first member, a cover member with flexibility which is arranged between the first member and the second member and comes in contact with at least the second member, and an indicator which is provided on the cover member and indicates in the cover member a change in state of a surface in contact with the second member.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 schematically shows an example of an endoscope apparatus.

FIG. 9 is a cross-sectional view showing an example of a cover member in a second embodiment.

FIG. 10 is a cross-sectional view showing another example of a concave portion and a convex portion provided on the cover member in the second embodiment.

FIG. 11 is a cross-sectional view showing yet another example of a concave portion and a convex portion provided on the cover member in the second embodiment.

FIG. 12 is a side view showing an example of a cover member in a third embodiment.

FIG. 13 is a cross-sectional view showing an example of the cover member in the third embodiment in a radial direction.

FIG. 14 is a side view showing an example of a cover member in a fourth embodiment.

DETAILED DESCRIPTION OF THE INVENTION

Figure 2:
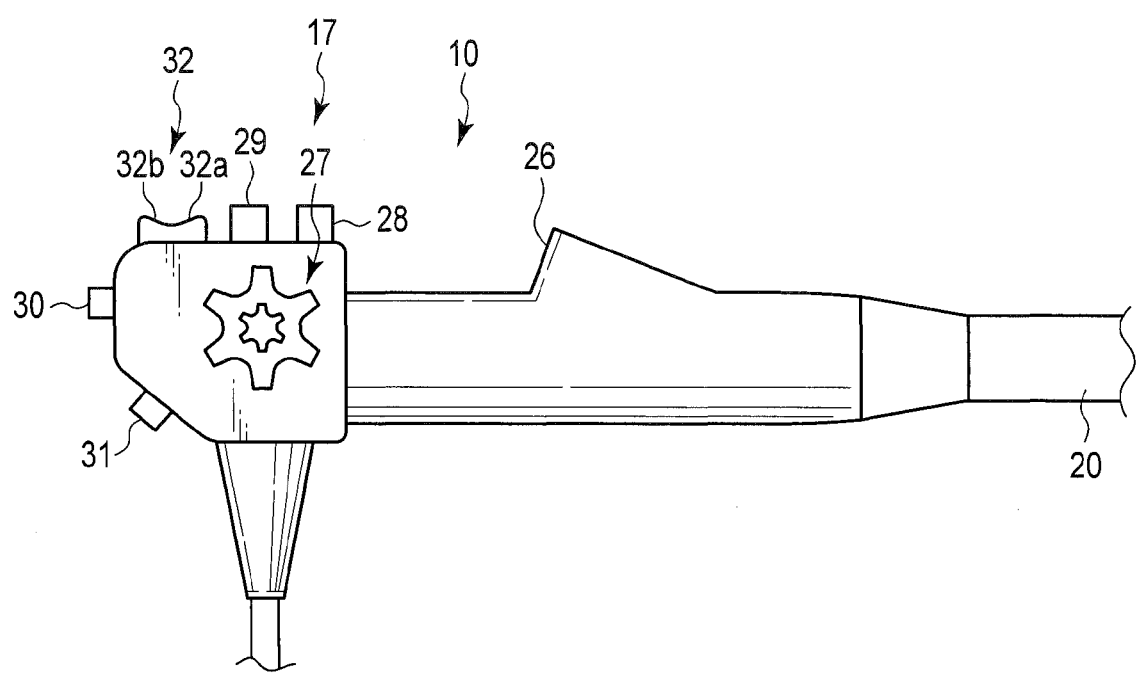
FIG. 2 shows a side surface of the opposite side of an operation section of the endoscope shown in FIG. 1.

FIG. 1 schematically shows an endoscope apparatus 1 which is an example of an insertion apparatus. The endoscope apparatus 1 comprises an endoscope system 10 comprising an endoscope 11, and a rotation unit 100 which is attached to the endoscope 11. The endoscope 11 is an example of insertion equipment which is inserted into an insertion object (for example, a serpentine intestinal canal such as a large intestine and a small intestine). The rotation unit 100 is an insertion assisting tool for assisting the endoscope 11 to be inserted into the insertion object.

The endoscope system 10 will be explained below. The endoscope system 10 comprises an endoscope 11, a control unit 12, a light source unit 13, an input unit 14, and a display unit 15.

The endoscope 11 comprises an insertion section 16 which is inserted into a lumen, and an operation section 17 which is provided on a proximal end side of the insertion section 16. The insertion section 16 is an elongated tubular body at a distal end side of the endoscope, and extends in a longitudinal axis direction. The insertion section 16 comprises a distal rigid portion 18, a bending portion 19 provided on the proximal end side of the distal rigid portion 18, and a flexible tube portion 20 provided on the proximal end side of the bending portion 19. In the distal rigid portion 18, an unillustrated illumination optical system, observation system, and image sensor, etc. are contained. The bending portion 19 is bent in a desired direction by a user controlling the operation section 17. The flexible tube portion 20 is free to bend, and, for example, bends along the bent shape inside the lumen, into which the insertion section 16 is inserted. Furthermore, inside the insertion section 16 extends a channel 21 for inserting therethrough a drive shaft 51 explained later on.

The operation section 17 is connected to the flexible tube portion 20 by a stopper 22. Across the inside of the insertion section 16 to the operation section 17 extends an optical fiber whose distal end is connected to the illumination optical system of the distal rigid portion 18 and an electric cable whose distal end is connected to the image sensor of the distal rigid portion 18, etc. These optical fibers and electric cables are accommodated in a universal cord 23 extending from the proximal end side of the operation section 17. At the proximal end of the universal cord 23 is provided a scope connector 24. The universal cord 23 is connected to the control unit 12 and the light source unit 13 via the scope connector 24. The operation section 17 is also provided with a driving source attachment port 25 communicating with the channel 21 inside the insertion section 16.

The control unit 12 is electrically connected to the endoscope 11, the light source unit 13, the input unit 14, and the display unit 15. The control unit 12 controls the operations of the endoscope 11 and peripheral device connected thereto (for example, the light source unit 13 and the later explained driving source 40). The control unit 12 also includes an unillustrated image processing unit. The light source unit 13 supplies illumination light to the illumination optical system arranged in the distal rigid portion 18 via the optical fiber. The input unit 14 is used for a user to input various instructions to the endoscope 11, etc. The display unit 15 displays an image obtained by the image sensor of the distal rigid portion 18 and image processed at the control unit 12, and operation information of the endoscope, etc.

FIG. 2 shows a side surface of the opposite side of the operation section 17 of the endoscope 11 shown in FIG. 1. The operation section 17 comprises a treatment tool insertion port 26 communicating with an unillustrated treatment tool channel extending inside the insertion section 16. The treatment tool insertion port 26 is arranged side by side with the driving source attachment port 25 shown in FIG. 1. Treatment tools such as an ultrasonic probe or biopsy forceps are inserted in the treatment tool insertion port 26.

As shown in FIG. 2, on the side surface of the operation section 17 is provided a bending operation knob 27 to which an operation for bending the bending portion 19 in a desired direction is input. In the inside of the operation section 17, a proximal end of an unillustrated bending wire for bending the bending portion 19 is connected to a shaft connected to the bending operation knob 27. The distal end of the bending wire is connected to the distal end portion of the bending portion 19. When a user rotates the bending operation knob 27, the bending wire connected thereto is pulled and causes the bending portion 19 to bend.

The operation section 17 is provided with various switches 28, 29, 30, and 31 such as an air feed/water feed switch, a suction switch, a photographing switch, and a change-over switch for switching over other predetermined functions. Furthermore, the operation section 17 is provided with a rotation operation input switch 32 to output to the control unit 12 a signal for rotating the rotation unit 100 around a center axis A1 of the insertion section 16. The rotation operation input switch 32 outputs a signal for causing the rotation unit 100 to rotate in a first direction (for example, clockwise) when a user, for example, presses a position indicated by reference numeral 32a, and outputs to the control unit 12 a signal for causing the rotation unit 100 to rotate in a second direction (for example, counter-clockwise) which is opposite to the first direction when a position indicated by reference numeral 32b is pressed.

With reference to FIG. 1 again, on the driving source attachment port 25 is attached a driving source 40 for causing the rotation unit 100 to rotate and drive around the center axis A1. The driving source 40 comprises a motor main body 41 which comprises a rotary shaft and a motor cable 42 which extends from the motor main body 41. The outer periphery of the motor main body 41 is retained on the driving source attachment port 25 by an unillustrated retaining ring. The rotary shaft of the motor main body 41 is connected to the drive shaft 51 explained later on. The proximal end of the motor cable 42 is electrically connected to the control unit 12.

Next, the rotation unit 100 will be explained below. The rotation unit 100 comprises a cylindrical tube main body 110. The tube main body 110 is a disposable tube which is detachably attached on the outer periphery of the insertion section 16. The tube main body 110 extends along a longitudinal axis A2. The longitudinal axis A2 is coaxial with the above-mentioned rotation center axis A1 when the tube main body 110 is attached to the insertion section 16. The tube main body 110 is provided with a lumen 111 through which the insertion section 16 may be inserted across the entire length.

The tube main body 110 is a flexible tube which is formed by a resin material such as polyurethane. On at least of part of the outer periphery of the tube main body 110 is formed a spiral fin 112 which is provided spirally clockwise as viewed in the proximal end direction. The spiral fin 112 is fixed to the tube main body 110 by adhesion or welding, etc., or is formed integrally with the tube main body 110, and protrudes in a radial direction from the outer periphery of the tube main body 110. The spiral fin 112 is formed of, for example, polyurethane, TPE, silicon, etc.

Figure 3:
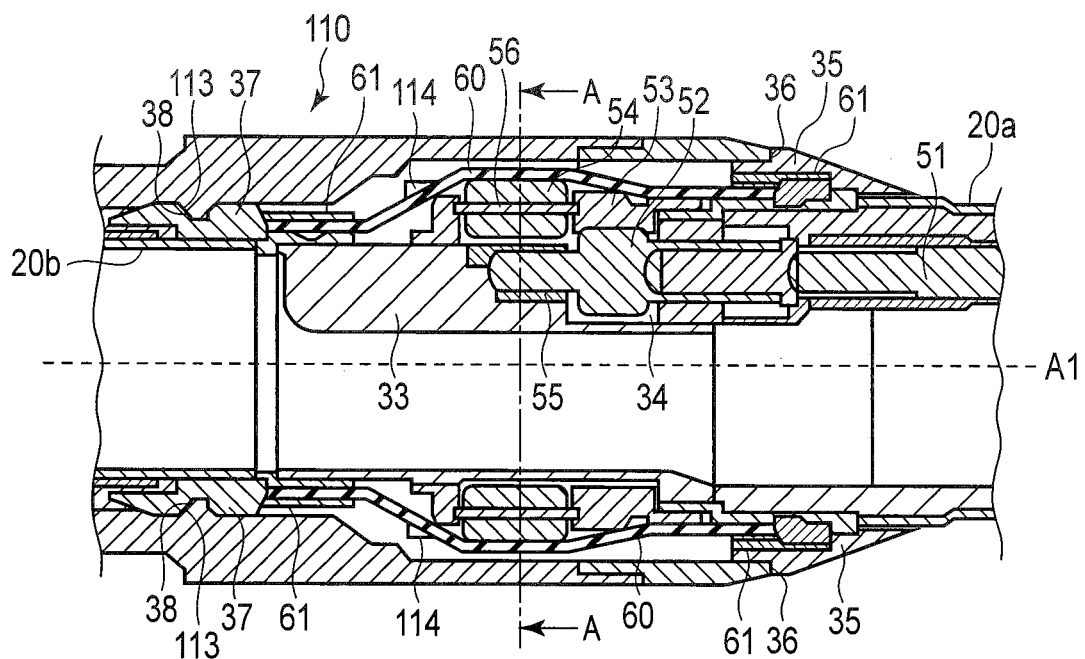
FIG. 3 shows a cross-section in a longitudinal axis direction including the driving force transmission mechanism.
Figure 4:
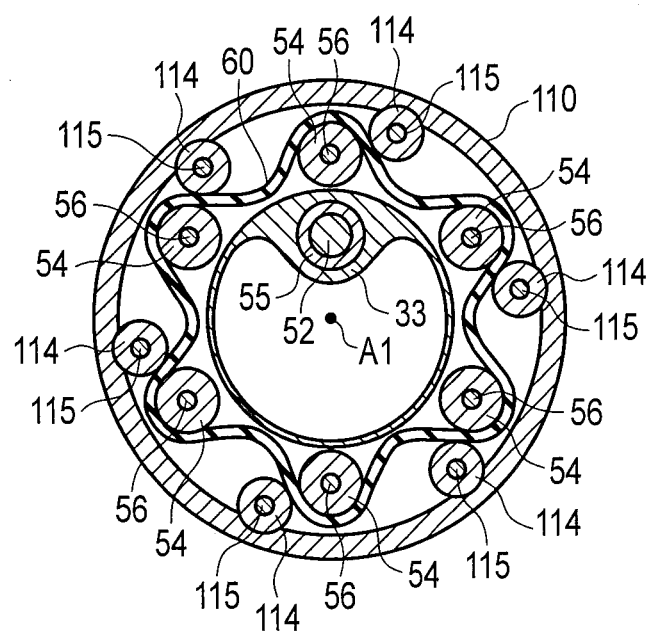
FIG. 4 is a cross-sectional view taken along line A-A in FIG. 3.

Next, the attachment of the tube main body 110 of the rotation unit 100 to the insertion section 16 (flexible tube portion 20), and matters regarding a driving force transmission mechanism 70 will be explained below. FIG. 3 shows a cross-section including the driving force transmission mechanism 70 for rotating and driving the tube main body 110 of the rotation unit 100 in a longitudinal axis direction. FIG. 4 is a cross-sectional view taken along line B-B in FIG. 3. As shown in FIG. 3, the flexible tube portion 20 has a first flexible tube portion 20a, and a second flexible tube portion 20b which is closer to the proximal end side of the flexible tube portion 20 than the first flexible tube portion 20a. The first flexible tube portion 20a and the second flexible tube portion 20b are connected by a rigid base portion 33 arranged therebetween. The base portion 33 forms a cavity 34 therein at the insertion section 16.

On the outer periphery of the base portion 33 is provided a stopper member 35. On the stopper member 35 is formed a receiving surface 36 to which the proximal end portion of the tube main body 110 abuts. This prevents the tube main body 110 from moving to the proximal end side when the tube main body 110 is attached to the insertion section 16. Furthermore, on the outer periphery of the base portion 33 is provided an annular engagement member 37 on which an annular groove 38 is formed. On the tube main body 110 is provided a pawl 113 which engages with the groove 38. When the tube main body 110 is attached to the insertion section 16, by engaging the groove 38 with the pawl 113, the movement of the tube main body 110 in the longitudinal direction is regulated.

On the insertion section 16 of the endoscope 11 is provided a flexible drive shaft 51, a rotation gear 52, an internal gear 53, and an internal roller (a first member) 54 with a circumferential surface. In FIG. 4, six internal rollers 54 are shown. However, the number of rollers is not limited to this.

As shown in FIG. 1, the proximal end of the drive shaft 51 is connected to the rotary shaft of the motor main body 41. The drive shaft 51 is arranged on the channel 21 which extends inside the insertion section 16. The drive shaft 51, for example, is obtained by multi-layers of superimposing what is obtained by knitting metal wires in a cylindrical net shape, or is formed of multi-layer wires obtained by superimposing right winding wire rods and left winding wire rods, and has rotation flowability with respect to the motor main body 41.

On the distal end of the drive shaft 51 is provided the rotation gear 52. The rotation gear 52 is arranged in the cavity 34 of the base portion 33, and has its proximal end side attached to the drive shaft 51, and its distal end side attached to the base portion 33 via the support member 55, respectively. When a rotative force around a longitudinal axis is applied to the proximal end of the drive shaft 51, the drive shaft 51 rotates the rotation gear 52. On the outer periphery of the rotation gear 52 is arranged an internal gear 53 which covers the base portion 33 and is attached to the outer periphery thereof. The external teeth of the rotation gear 52 are meshed with the internal teeth of the internal gear 53. The internal gear 53 is rotatable with respect to the base portion 33 about a longitudinal axis which is a revolution axis. On the internal gear 53 is attached a shaft 56 of the internal roller 54.

When the driving force from the motor main body 41 of the driving source 40 is transmitted to the drive shaft 51, the rotation gear 52 rotates, and the internal gear 53 being meshed with the rotation gear 52 rotates (revolves) in a circumferential direction. When the internal gear 53 rotates in a circumferential direction, the internal roller 54 rotates (revolves) in a circumferential direction.

On the outer periphery of the insertion section 16, the internal gear 53 and the internal roller 54 are covered with a cover 60 which is a cover member with flexibility. In other words, the cover 60 is formed cylindrically around its axis. The cover 60 is fixed (for example, a thread winding adhesion) to the base portion 33 by a cover fixing member 61 at both ends in the longitudinal axis direction. The cover 60 is a waterproof cover member which provides a barrier or a seal for protecting the internal gear 53, the internal roller 54, and other members arranged inside the insertion section 16 from the exterior environment (preventing intrusion of liquid inside a body cavity, water, or other liquids), and configures an outer coat of the insertion section 16. The cover 60 allows maintaining the inside of the insertion section 16 of the endoscope 11 to be watertight.

On the outside in the radial direction of the cover 60 is arranged an external roller 114 which is a second member configuring the driving force transmission mechanism 70. The external roller 114 is provided on the inner periphery of the tube main body 110 which is attached to the outer periphery of the insertion section 16. In FIG. 4, six internal rollers 54 and six external rollers 114 are arranged approximately in equal intervals on a circumference, and a state in which one internal roller 54 is in contact with one external roller 114 with the cover 60 interposed therebetween is shown. In other words, the inner periphery of the cover 60 is in contact with the internal roller 54, and the outer periphery of the cover 60 is in contact with the external roller 114.

When the driving source 40 is driven, the driving force is transmitted from the driving source 40 via the drive shaft 51, the rotation gear 52, and the internal gear 53, thereby, rotating (revolving) the internal roller 54 around the rotary axis A1 (revolution axis). In order to reduce friction caused by the cover 60, the internal roller 54 and the external roller 114 roll (rotate) on the cover 60. The rotation axis of each of the internal roller 54 and the external roller 114 is in parallel with the revolution axis of the internal roller 54 and the external roller 114. Since the cover 60 is fixed to the base portion 33 by the cover fixing member 61, it does not rotate with respect to the insertion section 16. However, rotary motion of the internal gear 53 from the internal roller 54 is transmitted to the external roller 114 which abuts the internal roller 54 via the cover 60. Accordingly, the driving force from the driving source 40 is transmitted to the rotation unit 100 from the driving force transmission mechanism 70 (the drive shaft 51, the rotation gear 52, the internal gear 53, the internal roller 54, the cover 60, and the external roller 114), and the rotation unit 100 is rotated and driven around the rotary axis A1. For example, when observing curved organs such as the small intestine or the large intestine, the rotation unit 100 advances while pushing the wall of the intestinal wall abutting the spiral fin 112 of the rotating tube main body 110 to the proximal end side, and assists the insertion section 16 to be inserted into a deep site.

In this manner, the endoscope apparatus 1 is provided with the driving force transmission mechanism 70 for rotating the rotation unit 100 attached to the outer periphery of the insertion section 16 around the axis of the insertion section 16. The driving force transmission mechanism 70 comprises a first member (the internal roller 54, or a bearing portion of the shaft 56 of the internal roller 54) which is connected to the driving source 40 and is moved in a circumferential direction about a predetermined axis (here, the longitudinal axis of the insertion section 16) by the driving force from the driving source 40. The driving force transmission mechanism 70 also comprises a second member (the external roller 114) which is capable of moving in the circumferential direction about the predetermined axis, is arranged to be positioned on a movement locus in the circumferential direction of the first member, and is moved in the predetermined axial direction by coming in contact with the first member when the first member is moved. The cover member (the cover 60) is arranged between the first member and the second member.

Figure 5:
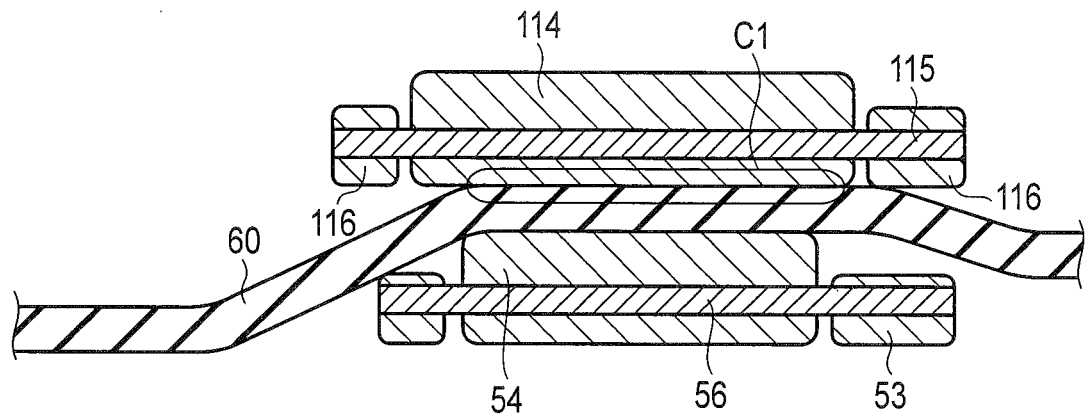
FIG. 5 is a cross-sectional view schematically showing a positional relationship between an internal roller, a cover member, and an external roller in a stationary state in a longitudinal axis direction.
Figure 6:
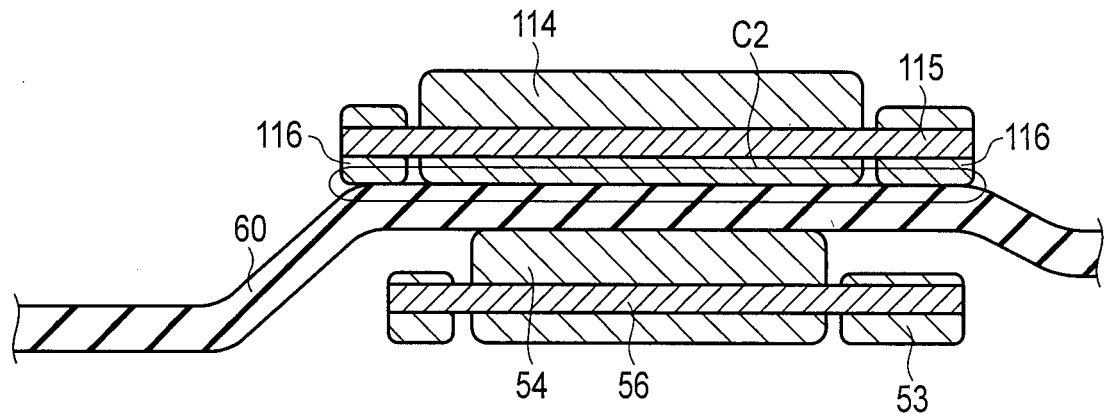
FIG. 6 is a cross-sectional view schematically showing the positional relationship between the internal roller, the cover member, and the external roller in a drive state in a longitudinal axis direction.

FIG. 5 and FIG. 6 are respectively cross-sectional views of schematically showing positional relationships between the internal roller 54, the cover 60, and the exterior roller 114 in a stationary state and a drive state in a longitudinal axis direction. The external roller 114 is supported by the shaft 115, on which both ends are provided a bearing portion 116. In the stationary state, the cover 60 consistently abuts the external roller 114 at an encircled region C1 shown in FIG. 5. Furthermore, when the rotation unit 100 is rotated by the driving force transmission mechanism 70, as shown in FIG. 6, since a force pulling the cover 60 towards a direction of the cover fixing member 61 on both sides of the cover 60 is applied to the cover 60, the cover 60 abuts not only the external roller 114, but also the bearing portion 116 (encircled region C2 in FIG. 6). Accordingly, the cover 60 wears away from the outer surface side of region C1 or region C2 by the friction occurring between the cover 60 and the external roller 114. Apparently, the cover 60 may also wear away by the friction occurring between the cover 60 and the internal roller 54; however, in the following, only the wear caused by the external roller 114 is considered.

As mentioned above, since the cover 60 serves to provide watertightness of the constituent members of the driving force transmission mechanism 70, etc. inside the insertion section 16 of the endoscope 11, it is necessary to prevent the occurrence of tearing caused by wear. It is also necessary to prevent tearing, etc. caused not only by wear, but also by cracks, etc. due to aging, etc.

The cover 60 for indicating a change in state caused by such tearing, etc. in each embodiment of the driving force transmission mechanism 70 of the present invention will be explained in detail below.

First Embodiment

Figure 7:
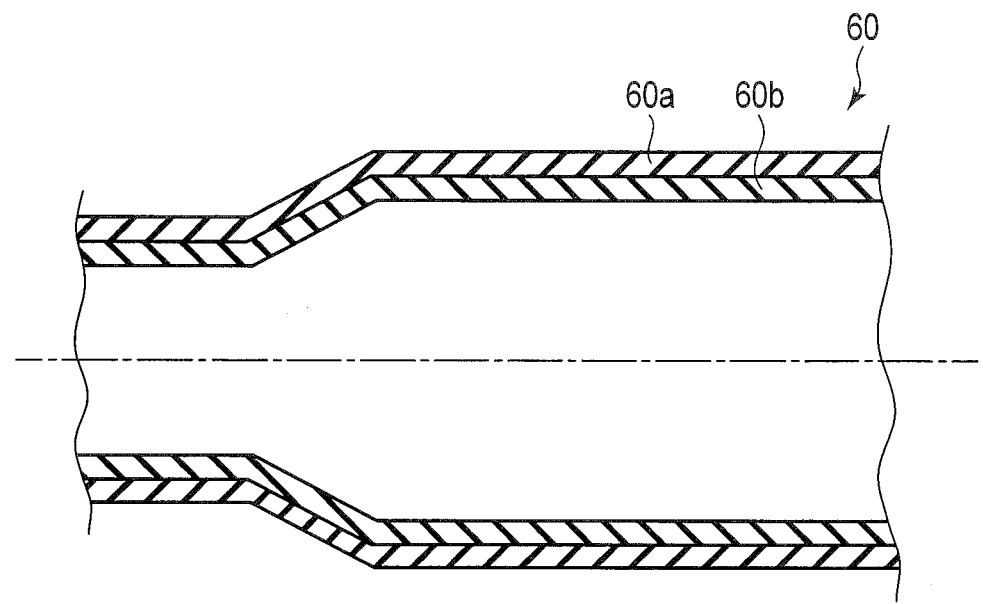
FIG. 7 is a cross-sectional view showing an example of a cover member in a first embodiment.

FIG. 7 is a cross-sectional view showing an example of a cover 60 provided in a driving force transmission mechanism 70 in a first embodiment. In the present embodiment, the cover 60 comprises a plurality of layers. In FIG. 7, the cover 60 is a double-layer cover comprising an outer side first layer 60*a* formed across the entire length of the cover 60, and an inner side second layer 60*b* in contact with the inner surface of the first layer 60*a* and formed across the entire length of the cover 60. The inner surface of the first layer 60*a* and the outer surface of the second layer 60*b* are, for example, adhered together across the entire surface thereof by an adhesive agent, etc. The materials of these layers are, for example, rubber, which is different in color between the first layer 60*a* and the second layer 60*b*. For example, the first layer 60*a* is black, and the second layer 60*b* is red.

When the cover 60 wears away by the friction between the cover 60 and a member (the external roller 114, the bearing portion 116, etc.) in contact with the outer surface of the cover 60, the cover 60 wears away from the first layer 60*a*. When the first layer 60*a* is completely scraped away by the wear, the second layer 60*b* underneath the first layer 60*a* is exposed. Since the color of the exposed second layer 60*b* is different from the color of the first layer 60*a*, a user confirms by sight that a color different from that of the first layer 60*a* has been exposed on the surface and detects the wear of the cover 60 before the cover 60 is completely scraped away and loses watertightness (at this time the second layer 60*b* still remains without being scraped away). In this manner, the user detects the wear of the cover 60 by looking at the outer surface of the cover 60 before and after usage, and deals with the replacement thereof, etc. as needed.

Other than the change in state caused by wear upon usage, sometimes, for example, when the endoscope apparatus 1 is not used for a long period of time, cracks, etc. may occur due to aging. In such case, the second layer 60*b* underneath will be exposed from portions where the first layer 60*a* has cracked. By inspecting the cover 60 prior to using the endoscope apparatus 1 after some time, the user would notice a color different from that of the first layer 60*a* being exposed on the surface, and detect the change in state of the cover 60. In a similar manner, in addition to the worn state, a fatigued state may also be detected from the change in state of the double-layer cover 60.

Figure 8:
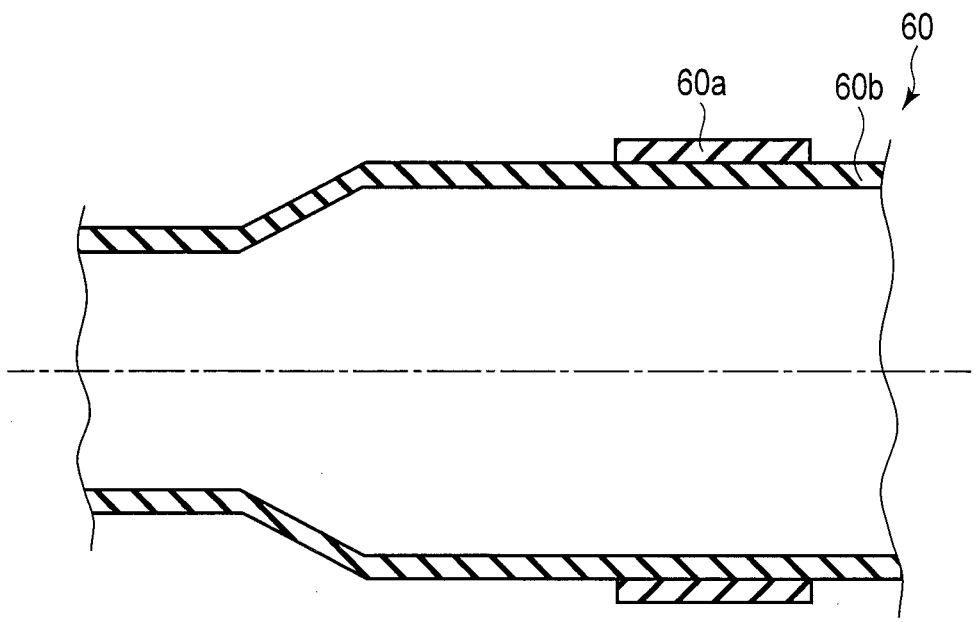
FIG. 8 is a cross-sectional view showing another example of the cover member in the first embodiment.

FIG. 8 is a diagram showing another example of the cover 60 in the first embodiment. In FIG. 8, the cover 60 is configured by the first layer 60*a* being provided on a part of the inner side second layer 60*b* formed across the entire length of the cover 60. The first layer 60*a* is provided at a position (a contact surface) where wear may easily occur by the abutment of other members (the external roller 114, the bearing portion 116, etc.). As shown in FIG. 8, a portion with a plurality of layers is not limited to the entire length of the cover 60; it may be a part of the cover 60 where it is easily worn.

In the above manner, the cover is provided with an indicator for detecting wear or aging thereof. The indicator in the present embodiment is what is obtained by forming a plurality of fabric in different colors in layers at the cover 60, that is, the first layer 60*a* and the second layer 60*b*. The indicator appears as the color of the cover 60 surface switching in accordance with the change in state thereof (wear degradation, aging degradation, fatigue degradation, etc.).

According to the present embodiment, the cover member comprising a plurality of layers in different colors functions as an indicator indicating the change in state. This allows a user to detect the change in state of the wear, etc. of the cover member by sight before the water-tightness of the cover member is lost, which would encourage the user to replace, etc. the cover member. By performing the replacement, etc., the performance of the member covered by the cover member, therefore the performance of the endoscope apparatus 1 would be maintained.

The number of layers configuring the cover 60 is not limited to two; therefore, the cover 60 may comprise three or more layers in different colors. In this case, the color to be exposed in accordance with the change in state of the wear of the cover 60, etc. may change, which would allow a user to detect the change in state of the cover 60 in stages. The second layer 60*b* exposed after the first layer 60*a* is worn may also have warning letters or design patterns, etc. drawn thereon to encourage a user to replace the cover 60, etc. This may encourage the user to replace covers, etc. in a more visual manner.

Second Embodiment

FIG. 9 is a cross-sectional view showing an example of a cover 60 provided on a driving force transmission mechanism 70 in a second embodiment. In the present embodiment, the cover 60 is formed of a single layer, and a convex portion 60*d* is formed on at least a part of an outer surface 60*c* of the cover 60. The convex portion 60*d* is a protrusion provided annularly on the outer periphery of the outer surface 60c, and is formed integrally with the cover 60. FIG. 9 shows three convex portions 60d arranged at intervals from each other. These convex portions 60d are formed at portions on the cover 60 which may be easily worn (portions abutting the external roller 114 and the bearing portion 116 (area C1 in FIG. 5, area C2 in FIG. 6)). Of course, the convex portion 60d may be formed across the entire length of the cover 60. The convex portion 60d functions as a tire slip sign, that is, an indicator that roughly indicates a usage limit.

In the present embodiment, when the cover 60 wears away by the friction occurring between the cover 60 and a member (the external roller 114, the bearing portion 116, etc.) in contact with the outer surface of the cover 60, the convex portion 60d is scraped away by the wear. When the convex portion 60d is scraped away and becomes approximately the same surface height as the outer surface 60c, a user detects by sight and touch that the convex portion 60d has disappeared by the wear. In this manner, the wear of the cover 60 is detected.

The shape and arrangement of the convex portion are not limited to those shown in FIG. 9. For example, the shape may be triangular shaped convex portions 60e and 60f with a pointed apex as shown in FIG. 10, or the arrangement may be such that the adjacent convex portions 60e are in contact with each other as shown in FIG. 10, or that the adjacent convex portions 60f are separated from each other as shown in FIG. 11. The number of convex portions is not limited to the number (three) shown in FIG. 9 to FIG. 11.

Furthermore, instead of the convex portion, or together with the convex portion, a concave portion may be provided by having a part of the outer surface 60c concaved. In this case, the concave portion is formed on a portion of the cover 60 which would not be easily worn (portions other than where the external roller 114 and the bearing portion 116 abut (areas C1 and C2)). When a surface of a portion other than where the concave portion is provided on the cover 60 is worn, the wear causes the portion other than the concave portion to become approximately the same surface height as the concave portion, thereby causing the concave portion to disappear. Therefore, a user detects by sight or touch that the convex has disappeared, and detects the wear of the cover 60.

According to the present embodiment, the convex portion or the concave portion (convex and concave shapes) provided annularly on the outer surface of the cover member functions as an indicator indicating the change in state. In other words, the indicator in the present embodiment is configured to change its surface shape by wear. This will allow a user to detect the change in state of the wear, etc. of the cover member by sight or touch before the watertightness of the cover member is lost, and encourage the replacement, etc. of the cover member. By performing replacement, etc., the performance of the member covered by the cover member would be maintained. Furthermore, in the present embodiment, since the cover member is formed by a single layer, two layers in different colors would not have to be prepared for the cover member as in the case of the first embodiment.

Third Embodiment

FIG. 12 is a side view showing an example of a cover 60 provided in the driving force transmission mechanism 70 in a third embodiment. FIG. 13 is a cross-sectional view showing an example of a cover 60 in a third embodiment in a radial direction. In the present embodiment, a protruding portion 60h is formed on at least a part of an outer surface 60g of the cover 60. The protruding portion 60h is provided along a longitudinal axis direction of the cover 60 on the outer periphery of the outer surface 60g. The protruding portion 60h is provided at a portion (portions abutting an external roller 114 and a bearing portion 116 (areas C1, C2)) that may be easily worn on the cover 60. Of course, this may be provided across the entire length of the cover 60. The protruding portion 60h is also an indicator that functions as a tire slip sign. The shape, number, and arrangement of the protruding portion 60h are also not limited to those shown in FIG. 12 and FIG. 13.

Also in the present embodiment, when the cover 60 is worn by the friction between the cover 60 and the member (the external roller 114, the bearing portion 116, etc.) in contact with the outer periphery of the cover 60, the protruding portion 60h is scraped away by the wear. When the protruding portion 60h is scraped away and becomes approximately the same height as the outer surface 60g, a user detects by sight and touch that the protruding portion 60h has disappeared by the wear. In this manner, the wear of the cover 60 is detected.

Also in the present embodiment, the protruding portion (concave and convex shapes) provided on the outer surface of the cover member along the longitudinal axis direction of the cover member functions as an indicator indicating the change in state. This will allow the user to detect the change in state of the wear, etc. of the cover member, and encourage the user to replace, etc. the cover member.

Fourth Embodiment

FIG. 14 is a side view showing an example of a cover 60 provided in a driving force transmission mechanism 70 in a fourth embodiment. In the present embodiment, a grid portion 60j is formed on an outer surface 60i of the cover 60. The grid portion 60j is provided in a circumferential direction and along a longitudinal axis direction on the outer surface 60i. The grid portion 60j also need not be on the entire length of the cover 60, however, and may be at a portion where the cover is easily worn. The grid portion 60j is also an indicator which functions as a slip sign.

Also in the present embodiment, when the cover 60 is worn by the friction between the cover 60 and the member (the external roller 114, the bearing portion 116, etc.) in contact with the cover 60, the grid portion 60j is scraped away by the wear. When the grid portion 60j is scraped away and becomes approximately the same height as an outer surface 60g, the user detects by sight and touch that the grid portion 60j has disappeared due to the wear. In this manner, the wear of the cover 60 is detected.

Also in the present embodiment, the grid portion 60j provided on the outer surface of the cover member in the circumferential direction and along the longitudinal axis direction of the cover member functions as an indicator indicating the change in state. This will allow a user to detect the change in state of the wear, etc. of the cover member, and encourage the user to replace, etc. the cover member.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A driving force transmission mechanism comprising:
a first member which is arranged inside an insertion section of an insertion apparatus extending along a predetermined axis, is connected to a driving source and is moved in a circumferential direction about a predetermined axis by a driving force from the driving source;
a second member which is movable in a circumferential direction about the predetermined axis on an insertion assisting tool attached to an outer periphery of the insertion section, and is arranged to be positioned on a movement locus in the circumferential direction of the first member;
a cover member with flexibility which configures an outer coat of the insertion section, and is arranged between the first member and the second member to come in contact with at least the second member; and
an indicator which is provided on the cover member and indicates in a change in state of a surface of the cover member in contact with the second member.

2. The driving force transmission mechanism according to claim 1, wherein the first member and the second member are respectively arranged to be revolvable in the predetermined axial direction.

3. The driving force transmission mechanism according to claim 2, wherein the first member and the second member are arranged to be rotatable in each of their rotation axis directions.

4. The driving force transmission mechanism according to claim 3, wherein each of the rotation axes of the first member and the second member is in parallel with the predetermined axis.

5. The driving force transmission mechanism according to claim 4, wherein the first member and the second member are in a roller shape comprising a circumferential surface in each of their rotation axis directions.

6. The driving force transmission mechanism according to claim 1, wherein the cover member is formed cylindrically comprising an inner surface and an outer surface in the predetermined axial direction, the first member being in contact with the inner surface and the second member being in contact with the outer surface.

7. The driving force transmission mechanism according to claim 1, wherein the indicator is arranged on a surface in contact with the second member.

8. The driving force transmission mechanism according to claim 1, wherein the indicator indicates a worn state of the surface in contact with the second member on the cover member.

9. The driving force transmission mechanism according to claim 1, wherein the indicator indicates a fatigued state of the surface in contact with the second member on the cover member.

10. The driving force transmission mechanism according to claim 1, wherein the indicator indicates a degradation state of the cover member.

11. The driving force transmission mechanism according to claim 1, wherein the indicator indicates an aging state of the cover member.

12. The driving force transmission mechanism according to claim 1, wherein the indicator indicates a change in state of the cover member by the color of the surface switching over.

13. The driving force transmission mechanism according to claim 12, wherein the indicator is configured by forming the cover member in a plurality of fabric layers in different colors.

14. The driving force transmission mechanism according to claim 1, wherein a surface in contact with the second member on the cover member is configured to change its surface shape by being worn.

15. The driving force transmission mechanism according to claim 14, wherein a surface in contact with the second member on the cover member has a concavo-convex shape formed thereon.

* * * * *